US007252988B2

(12) United States Patent
Saint-Ramon et al.

(10) Patent No.: US 7,252,988 B2
(45) **Date of Patent: *Aug. 7, 2007**

(54) STRAW FOR THE CONSERVATION OF SMALL QUANTITIES OF SUBSTANCES, IN PARTICULAR BIOLOGICAL LIQUIDS

(75) Inventors: Jean-Gérard Saint-Ramon, L'Aigle (FR); Francis Lesieur, Saint-Michel Thubeuf (FR)

(73) Assignee: IMV Technologies, L'Aigle (FR)

( * ) Notice: Subject to any disclaimer, the term of this patent is extended or adjusted under 35 U.S.C. 154(b) by 768 days.

This patent is subject to a terminal disclaimer.

(21) Appl. No.: 10/139,629

(22) Filed: May 7, 2002

(65) Prior Publication Data

US 2002/0188222 A1 Dec. 12, 2002

(30) Foreign Application Priority Data

May 7, 2001 (FR) .................................. 01 06081

(51) Int. Cl.
*C12M 1/24* (2006.01)
*C12M 3/00* (2006.01)

(52) U.S. Cl. .............................. 435/307.1; 435/304.1; 435/309.1; 422/100; 422/102; 73/864.02; 73/864.03; 220/364; 600/33

(58) Field of Classification Search ............. 435/284.1, 435/304.1, 304.2, 307.1, 309.1; 422/100, 422/102, 916, 917; 73/864.02, 864.03; 215/261; 220/364, 371; 600/573, 33–35
See application file for complete search history.

(56) References Cited

U.S. PATENT DOCUMENTS

| | | | | |
|---|---|---|---|---|
| 2,850,033 | A * | 9/1958 | Hartle | 137/197 |
| 3,750,688 | A * | 8/1973 | Hall et al. | 137/2 |
| 4,500,670 | A * | 2/1985 | McKinley et al. | 524/445 |
| 4,925,060 | A * | 5/1990 | Gustafson | 220/371 |
| 5,279,606 | A | 1/1994 | Haber et al. | |
| 5,283,170 | A * | 2/1994 | Cassou et al. | 435/1.3 |
| 6,203,489 | B1 | 3/2001 | Mori et al. | |
| 6,300,125 | B1 * | 10/2001 | Saint-Ramon et al. | 435/307.1 |

FOREIGN PATENT DOCUMENTS

| | | | |
|---|---|---|---|
| EP | 0917862 | A1 | 5/1999 |
| FR | 2753367 | A1 | 3/1998 |
| GB | 669265 | | 4/1952 |
| GB | 1192946 | A1 | 5/1970 |
| GB | 1299934 | A1 | 12/1972 |
| JP | 07-22717 | | 4/1995 |
| JP | 08-862 | | 5/1996 |
| WO | WO 8700439 | A1 * | 1/1987 |

* cited by examiner

*Primary Examiner*—William H. Beisner
(74) *Attorney, Agent, or Firm*—Browdy and Neimark, PLLC

(57) ABSTRACT

A straw (1) for the conservation of small quantities of substances, in particular biological substances, having a segment of tube provided inside one end with a stopper including gel powder, characterized in that a proportion of the gel powder is replaced with dispersed nonabsorbent material, the stopper thus having a mixture of gel powder and dispersed nonabsorbent material.

5 Claims, 2 Drawing Sheets

Figure 1:
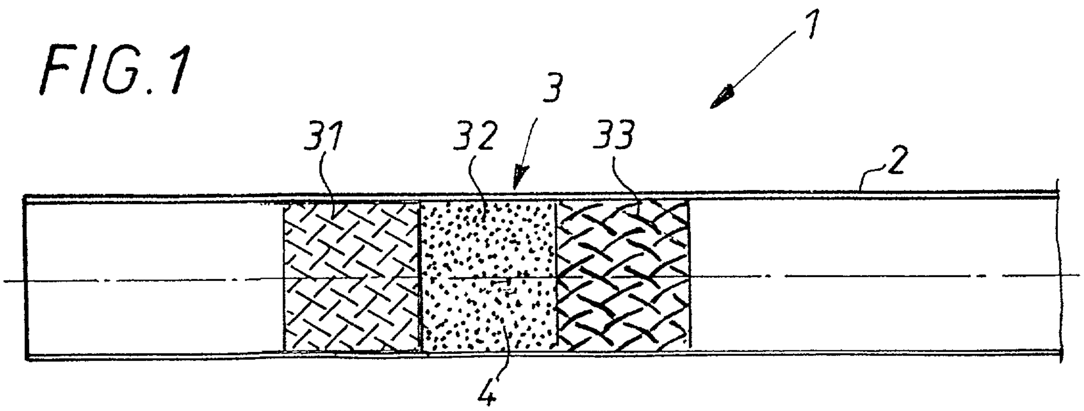

STRAW FOR THE CONSERVATION OF SMALL QUANTITIES OF SUBSTANCES, IN PARTICULAR BIOLOGICAL LIQUIDS

The present invention relates to a straw for the conservation of small quantities of substances, in particular biological liquids.

This type of straw, which is known as a “French straw”, was disclosed for the first time in French patent No. 995 878.

Straws manufactured in accordance with the above patent and used until now have a three-part stopper consisting of two plugs of a fibrous substance with a powder between them that on contact with a liquid is converted into an impermeable gel or paste adhering to the wall of the tube to create a sealed stopper.

Straws with a three-part stopper developed and marketed by the applicant are entirely satisfactory. Nevertheless, some absorption of the liquid contained in the straw has been noted, although it is very slight, of the order of 7%.

One solution to the above problem that has been proposed is to replace the three-part stopper with a metal or rigid plastics material ball. This solution has not proved satisfactory because, although absorption of the liquid contained in the straw has been eliminated, new and unacceptable difficulties have arisen, the stopper no longer providing a liquid seal.

The patent FR-A-2 753 367 proposes a straw including a three-part stopper comprising a hydrogel powder between two plugs, namely an external plug and an internal plug, said straw being characterized in that the length of the external plug is at least twice the length of the internal plug. According to the above patent, absorption of the liquid contained in the straw is only very slightly reduced compared to that observed in a straw fitted with a standard three-part stopper.

An object of the present invention is to provide a straw fitted with a stopper that absorbs only a small quantity of a liquid contained in the straw. To be more precise, an object of the invention is to provide a straw fitted with a stopper that absorbs a quantity of a liquid contained therein at most equal to approximately 4%.

Other objects and advantages of the invention will become apparent on reading the following description.

In accordance with the above object, the present invention provides a straw for the conservation of small quantities of substances, in particular biological substances, comprising a segment of tube provided inside one end with a stopper including gel powder, characterized in that a proportion of the gel powder is replaced with dispersed nonabsorbent material, said stopper thus comprising a mixture of gel powder and dispersed nonabsorbent material.

The gel powder is converted on contact with a liquid into an impermeable gel or paste adhering to the wall of the tube to create a sealed stopper.

The gel powder can be alginate or polyvinyl alcohol, for example.

In accordance with the invention, a proportion of the gel powder is replaced with the dispersed nonabsorbent material.

The nonabsorbent material can be glass, PVC, diatoms, perlites, etc., for example.

The nonabsorbent material must be dispersed.

The particle size of the nonabsorbent material must be close to that of the gel powder.

The particle size of the gel powder used is easy for the person skilled in the art to determine from the nature of said gel powder.

The nonabsorbent material takes the form of balls, for example.

The balls have an average diameter from approximately 50 μm to approximately 300 μm, for example.

The nonabsorbent material can equally take the form of small flakes or fragments.

In accordance with the invention, from approximately 10% to approximately 50% of the gel powder is replaced with the dispersed nonabsorbent material.

In accordance with the invention, the straw can be fitted with a three-part or one-piece stopper.

The three-part stopper comprises an external part that is not in direct contact with the liquid contained in the straw and an internal part that is in contact with the liquid contained in the straw, with an intermediate part containing the gel powder between them.

The three parts may be substantially the same length or different lengths.

In a first embodiment, the straw is fitted with a standard three-part stopper. The stopper comprises two fibrous substance plugs with a gel powder between them. In accordance with the invention, a proportion of the gel powder of the stopper is replaced with the dispersed nonabsorbent material.

In this first embodiment, the external part is made of a standard fibrous substance and the internal part is made of a standard fibrous substance.

The external and internal parts can take the form of a braid.

The intermediate part comprises a mixture of gel powder and dispersed nonabsorbent material.

In the first embodiment, the straw for the conservation of small quantities of substances, in particular biological substances, comprises a segment of tube provided inside one end with a stopper comprising an external part and an internal part with an intermediate part including the gel powder between them. It is characterized in that the intermediate part comprises a mixture of gel powder and dispersed nonabsorbent material.

In a second embodiment of the invention, the stopper of the straw according to the invention is a three-part stopper and comprises a thermoplastics material core sheathed with filaments constituting a sheath.

In a first instance of this second embodiment, the three-part stopper comprises an external part comprising a fibrous substance braid, an internal part comprising a thermoplastics material core sheathed with filaments constituting a sheath, and an intermediate part comprising gel powder a proportion of which, in accordance with the invention, is replaced with dispersed nonabsorbent material.

In other words, in the first and second embodiments, the intermediate part comprises a mixture of gel powder and dispersed nonabsorbent material.

In a second instance of the second embodiment, the three-part stopper comprises an external part comprising a fibrous substance braid, an internal part comprising a thermoplastics material core sheathed with filaments constituting a sheath, said core incorporating a bore, and an intermediate part comprising gel powder a proportion of which, in accordance with the invention, is replaced with dispersed nonabsorbent material.

Once again, the intermediate part comprises a mixture of gel powder and dispersed nonabsorbent material.

In a third instance of the second embodiment, the three-part stopper comprises an external part comprising a fibrous substance braid, an internal part comprising a thermoplastics material core sheathed with filaments constituting a sheath, said core including a central braid, and an intermediate part comprising gel powder a proportion of which, in accordance with the invention, is replaced with dispersed nonabsorbent material.

The intermediate part therefore comprises a mixture of gel powder and dispersed nonabsorbent material.

In a third embodiment of the invention, the stopper is a one-piece stopper.

In a first instance of the third embodiment, the one-piece stopper comprises a thermoplastics material core sheathed with filaments constituting a sheath impregnated with a gel powder a proportion of which, in accordance with the invention, is replaced with dispersed nonabsorbent material.

In a second instance of the third embodiment, the one-piece stopper comprises a thermoplastics material core sheathed with filaments constituting a sheath and comprising a central braid impregnated with gel powder a proportion of which, in accordance with the invention, is replaced with dispersed nonabsorbent material.

In the case of a three-part stopper, the total length of the stopper is from approximately 7 mm to approximately 14 mm.

The length of the external part is from approximately 3 mm to approximately 14 mm.

The length of the internal part is from approximately 2 mm to approximately 5 mm.

The length of the intermediate part is from approximately 1.5 mm to approximately 5 mm.

The quantity of gel powder that must be incorporated into the stopper of the straw before the implementation of the invention depends on the type of stopper and is known to the person skilled in the art.

In all cases, in accordance with the invention, a proportion of the gel powder must be replaced with dispersed nonabsorbent material.

The proportion of gel powder replaced with dispersed nonabsorbent material is from approximately 10% to approximately 50% and depends on the type of stopper. The person skilled in the art will in each case easily be able to determine the proportion of gel powder to be replaced with dispersed nonabsorbent material to obtain a straw with a sealed stopper and reduced absorption of liquid.

The straw of the invention provides a good seal and very little absorption of the liquid contained therein, of the order of 4% and even less.

Figure 2:
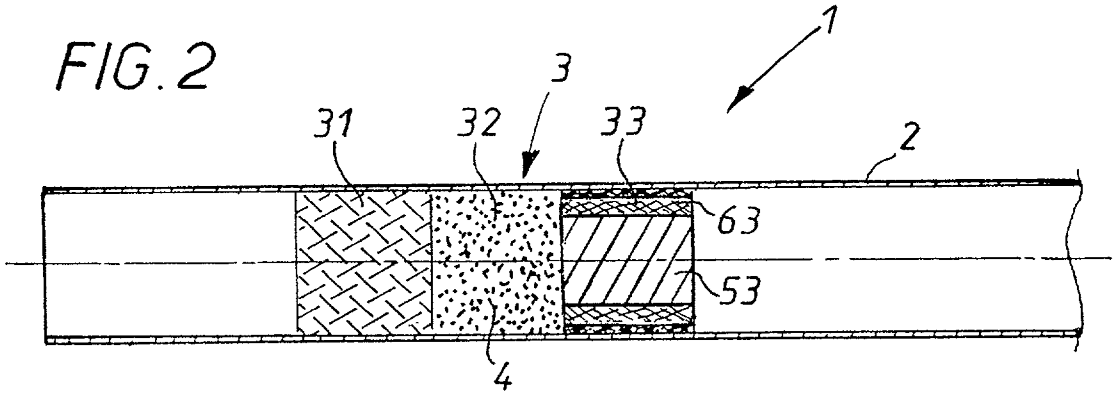
Figure 3:
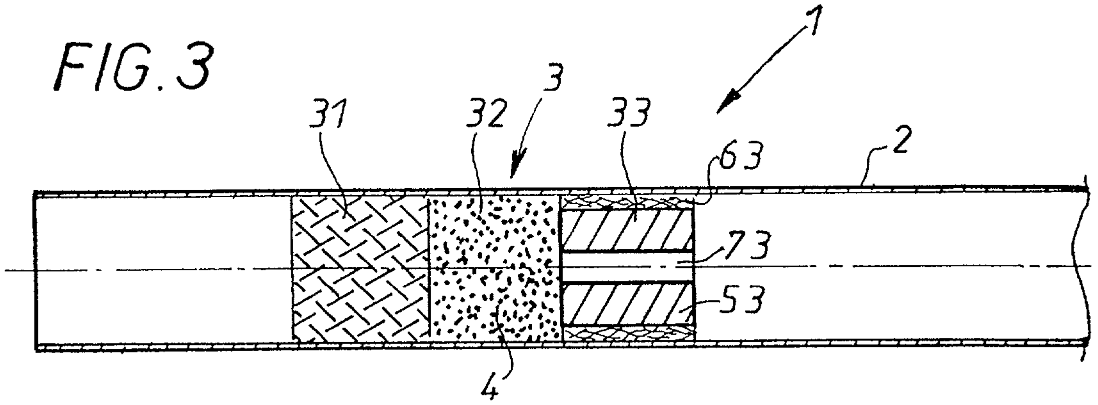
Figure 4:
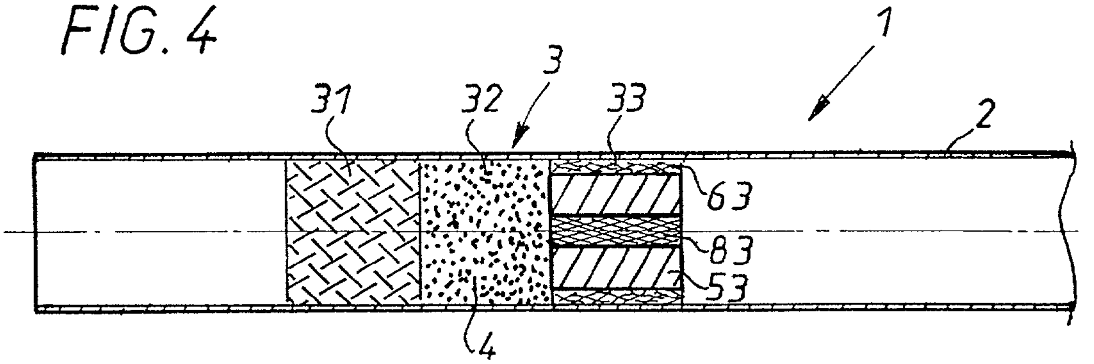
Figure 5:
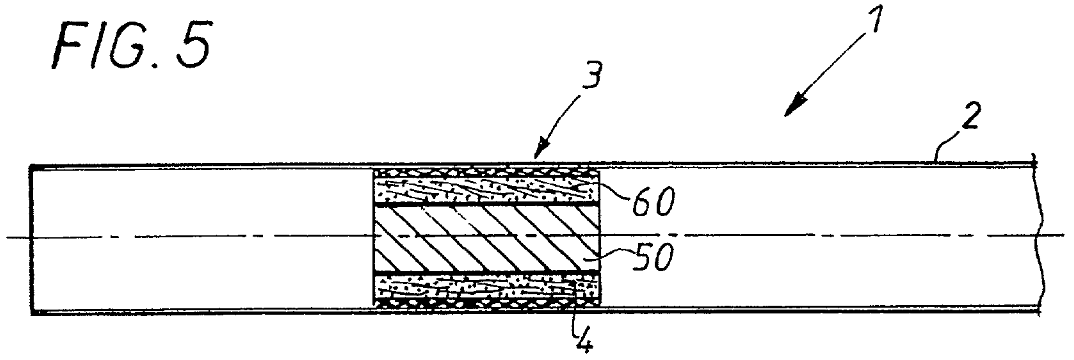
Figure 6:
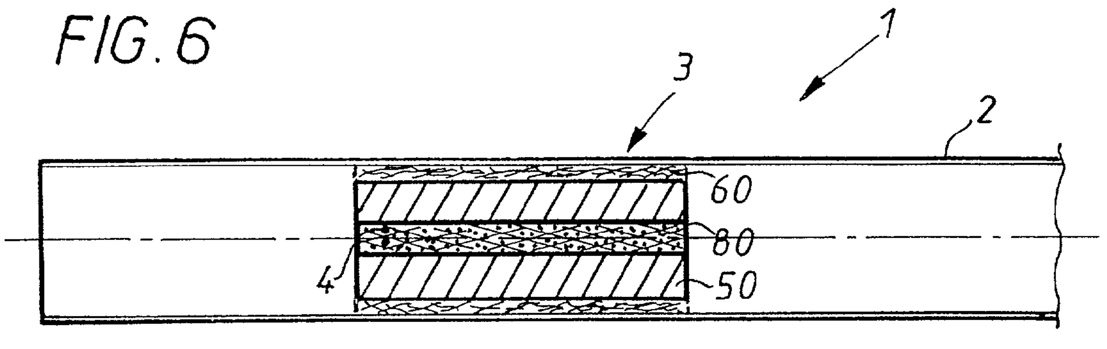

The invention will be described in more detail but in a nonlimiting manner with reference to the accompanying drawings, in which:

FIG. 1 is a partial view of a first embodiment of a straw of the invention,

FIG. 2 is a partial view of a first instance of a second embodiment of a straw of the invention, FIG. 3 is a partial view of a second instance of the second embodiment of a straw of the invention, FIG. 4 is a partial view of a third instance of the second embodiment of a straw of the invention, FIG. 5 is a partial view of a first instance of a third embodiment of a straw of the invention, FIG. 6 is a partial view of a first instance of the third embodiment of a straw of the invention.

Referring to FIG. 1, the straw 1 comprises a segment of tube 2 fitted at one end with a three-part stopper 3.

The external part 31, which is not in contact with the liquid contained in the straw, is a fibrous substance braid.

The internal part 33, which is in contact with the liquid contained in the straw, is a fibrous substance braid.

The intermediate part 32 comprises a mixture 4 of gel powder and dispersed nonabsorbent material.

Referring to FIG. 2, the straw 1 comprises a segment of tube 2 fitted at one end with a three-part stopper 3.

The external part 31, which is not in contact with the liquid contained in the straw, is a fibrous substance braid.

The internal part 33, which is in contact with the liquid contained in the straw, comprises a thermoplastics material core 53 sheathed with filaments constituting a sheath 63.

The intermediate part 32 comprises a mixture 4 of gel powder and dispersed nonabsorbent material.

Referring to FIG. 3, the straw 1 comprises a segment of tube 2 fitted at one end with a three-part stopper 3.

The external part 31, which is not in contact with the liquid contained in the straw, is a fibrous substance braid.

The internal part 33, which is in contact with the liquid contained in the straw, comprises a thermoplastics material core 53 sheathed with filaments constituting a sheath 63. The core 53 includes a bore 73.

The intermediate part 32 comprises a mixture 4 of gel powder and dispersed nonabsorbent material.

Referring to FIG. 4, the straw 1 comprises a segment of tube 2 fitted at one end with a three-part stopper 3.

The external part 31, which is not in contact with the liquid contained in the straw, is a fibrous substance braid.

The internal part 33, which is in contact with the liquid contained in the straw, comprises a thermoplastics material core 53 sheathed with filaments constituting a sheath 63. The core 53 includes a central braid 83.

The intermediate part 32 comprises a mixture 4 of gel powder and dispersed nonabsorbent material.

Referring to FIG. 5, the straw 1 comprises a segment of tube 2 fitted at one end with a three-part stopper 3.

The stopper 3 comprises a thermoplastics material core 50 sheathed with filaments constituting a sheath 60. The filaments of the sheath 60 are impregnated with a mixture 4 of gel powder and dispersed nonabsorbent material.

Referring to FIG. 6, the straw 1 comprises a segment of tube 2 fitted at one end with a three-part stopper 3. The stopper 3 comprises a thermoplastics material core 50 sheathed with filaments constituting a sheath 60 comprising a central braid 80 of synthetic filaments impregnated with a mixture 4 of gel powder and dispersed nonabsorbent material.

The person skilled in the art will understand that although the invention is described and illustrated with respect to particular embodiments, many variants thereof can be envisaged that remain within the scope of the invention as defined by the accompanying claims.

The invention claimed is:

1. A straw for the conservation of small quantities of substances, in particular biological substances, comprising a segment of tube provided inside one end with a stopper including a sealing composition comprising gel powder and dispersed nonabsorbent material, and at least one of a braid and a sheath, wherein said gel powder is selected to form an impermeable seal upon absorbing a quantity of the substance and said dispersed nonabsorbent material is selected to reduce the amount of the substance that must be absorbed to form the impermeable seal, in comparison with the amount of the substance that must be absorbed by a corresponding sealing composition consisting only of said gel powder to form the impermeable seal, wherein said stopper is a three-part stopper comprising an external part that is not in direct contact with the substance contained in said straw and an internal part that is in contact with the substance contained in said straw, with an intermediate part constituted by said sealing composition between said external and internal parts, and wherein said at least one of a braid and a sheath comprises a braid and a sheath, said external part comprises a fibrous substance constituting said braid, and said internal part comprises a solid core consisting of thermoplastics material sheathed with filaments constituting said sheath.

2. A straw for the conservation of small quantities of substances, in particular biological substances, comprising a segment of tube provided inside one end with a stopper including a sealing composition comprising gel powder and dispersed nonabsorbent material, and at least one of a braid and a sheath, wherein said gel powder is selected to form an impermeable seal upon absorbing a quantity of the substance and said dispersed nonabsorbent material is selected to reduce the amount of the substance that must be absorbed to form the impermeable seal, in comparison with the amount of the substance that must be absorbed by a corresponding sealing composition consisting only of said gel powder to form the impermeable seal, wherein said stopper is a three-part stopper comprising an external part that is not in direct contact with the substance contained in said straw and an internal part that is in contact with the substance contained in said straw, with an intermediate part constituted by said sealing composition between said external and internal parts, and wherein said at least one of a braid and a sheath comprises a braid and a sheath, said external part comprises a fibrous substance constituting said braid, said internal part comprises a solid core consisting of thermoplastics material sheathed with filaments constituting said sheath, said core including a bore.

3. A straw for the conservation of small quantities of substances, in particular biological substances, comprising a segment of tube provided inside one end with a stopper including a sealing composition comprising gel powder and dispersed nonabsorbent material, and at least one of a braid and a sheath, wherein said gel powder is selected to form an impermeable seal upon absorbing a quantity of the substance and said dispersed nonabsorbent material is selected to reduce the amount of the substance that must be absorbed to form the impermeable seal, in comparison with the amount of the substance that must be absorbed by a corresponding sealing composition consisting only of said gel powder to form the impermeable seal, wherein said stopper is a three-part stopper comprising an external part that is not in direct contact with the substance contained in said straw and an internal part that is in contact with the substance contained in said straw, with an intermediate part constituted by said sealing composition between said external and internal parts, and said at least one of a braid and a sheath comprises a braid and a sheath, said external part comprises a fibrous substance constituting said braid, said internal part comprises a solid core consisting of thermoplastics material sheathed with filaments constituting said sheath, said core including a central braid.

4. A straw for the conservation of small quantities of substances, in particular biological substances, comprising a segment of tube provided inside one end with a stopper including a sealing composition comprising gel powder and dispersed nonabsorbent material, and at least one of a braid and a sheath, wherein said gel powder is selected to form an impermeable seal upon absorbing a quantity of the substance and said dispersed nonabsorbent material is selected to reduce the amount of the substance that must be absorbed to form the impermeable seal, in comparison with the amount of the substance that must be absorbed by a corresponding sealing composition consisting only of said gel powder to form the impermeable seal, and wherein said at least one of a braid and a sheath comprises a sheath, and said stopper is a one-piece stopper comprising a solid core consisting of thermoplastics material sheathed with filaments constituting said sheath impregnated with said sealing composition.

5. A straw for the conservation of small quantities of substances, in particular biological substances, comprising a segment of tube provided inside one end with a stopper including a sealing composition comprising gel powder and dispersed nonabsorbent material, and at least one of a braid and a sheath, wherein said gel powder is selected to form an impermeable seal upon absorbing a quantity of the substance and said dispersed nonabsorbent material is selected to reduce the amount of the substance that must be absorbed to form the impermeable seal, in comparison with the amount of the substance that must be absorbed by a corresponding sealing composition consisting only of said gel powder to form the impermeable seal, wherein said at least one of a braid and a sheath comprises a braid and a sheath, said stopper is a one-piece stopper comprising a solid core consisting of thermoplastics material sheathed with filaments constituting said sheath and said braid is a central braid impregnated with at least a portion of said sealing composition.

* * * * *